United States Patent [19]

Lee

[11] Patent Number: 4,713,053
[45] Date of Patent: Dec. 15, 1987

[54] METHOD AND APPARATUS FOR PERFORMING SUCTION LIPECTOMY

[76] Inventor: Hans Lee, 526 Sheridan Cir., Charleston, W. Va. 25314

[21] Appl. No.: 887,040
[22] PCT Filed: May 6, 1985
[86] PCT No.: PCT/US85/00814
§ 371 Date: Jan. 3, 1986
§ 102(e) Date: Jan. 3, 1986
[87] PCT Pub. No.: WO85/05024
PCT Pub. Date: Nov. 21, 1985

Related U.S. Application Data

[63] Continuation-in-part of Ser. No. 607,714, May 7, 1984, Pat. No. 4,596,553, and a continuation-in-part of Ser. No. 651,720, Sep. 18, 1984, Pat. No. 4,627,834.

[51] Int. Cl.$^4$ .................. A61M 31/00; A61M 5/00
[52] U.S. Cl. .................. 604/49; 604/117; 604/264; 604/902
[58] Field of Search .................. 604/49–51, 604/73, 19, 21, 117, 264, 902; 128/759

[56] References Cited

U.S. PATENT DOCUMENTS

| | | | |
|---|---|---|---|
| 390,177 | 9/1888 | Lee | 604/280 |
| 504,352 | 9/1893 | Heysinger | 30/286 |
| 1,698,331 | 1/1929 | Gunter | 433/94 |
| 1,749,919 | 3/1930 | Mierley | 128/305 |
| 2,198,666 | 4/1940 | Gruskin | 604/117 |
| 2,338,800 | 1/1944 | Burke | 604/117 |
| 2,545,115 | 3/1951 | Son | 604/117 |
| 2,705,949 | 4/1955 | Silverman | 604/117 X |
| 2,715,899 | 8/1955 | MacLean | 128/758 |
| 2,876,539 | 3/1959 | Ford | 30/283 |
| 3,920,001 | 11/1975 | Edwards | 128/765 |
| 4,235,234 | 11/1980 | Whitney et al. | 604/117 |
| 4,318,414 | 3/1982 | Schuster | 128/759 |
| 4,536,180 | 8/1985 | Johnson | 604/268 |
| 4,596,553 | 6/1986 | Lee | 604/49 |

Primary Examiner—Ferris H. Lander
Attorney, Agent, or Firm—Lowe, Price, LeBlanc, Becker & Shur

[57] ABSTRACT

A cannula is provided with a guide bar extending in spaced, parallel relationship to the cannula. Adjacent and overlying a hole formed in the cannula tip through which suction is applied to surgically aspirate fatty tissue is a guide surface adapted to contact and slide against the skin of a patient while the cannula tip is manually directed by the surgeon through the fatty tissue in reciprocating strokes. The guide surface, which may be a pair of wheels, maintains the tip at a constant depth within the tissue so that, upon completion of suction lipectomy, a desired amount of fatty tissue is surgically aspirated while leaving an even thickness layer of tissue in tact. A new surgical procedure for performing suction lipectomies with the guided cannula of the invention is also disclosed. In accordance with a second embodiment of the invention, the guide bar includes an elevated portion spaced a greater distance from the cannula and a forward end of the guide bar having the guide surface. The elevated portion is manually engageable to permit two-handed reciprocating movement of the cannula by the surgeon and to allow the surgeon to contact the patient's skin beneath the elevated portion to assist the cannula in the surgical procedure.

16 Claims, 18 Drawing Figures

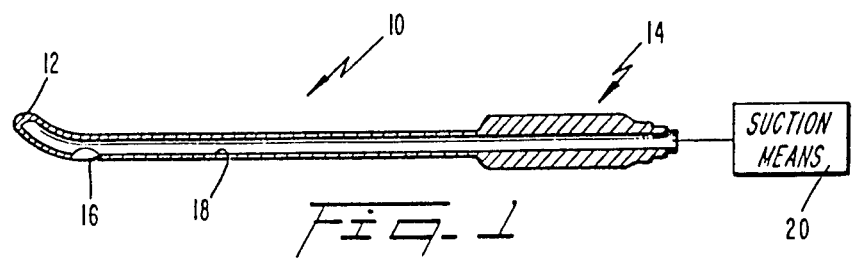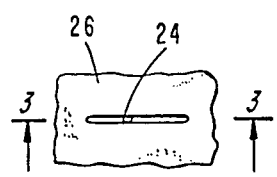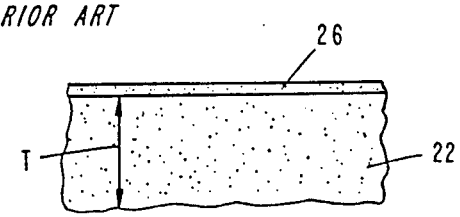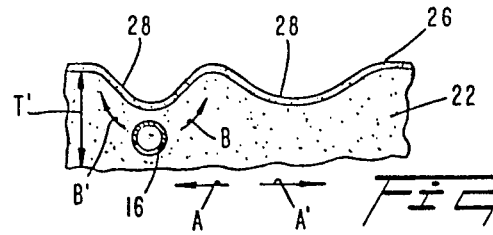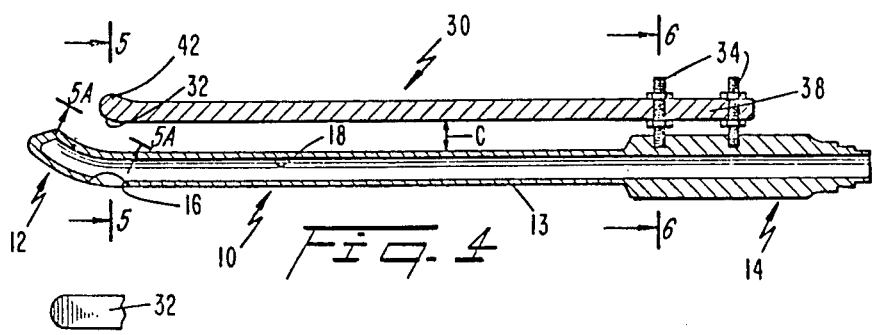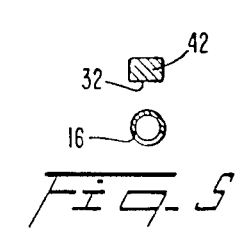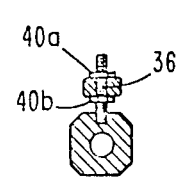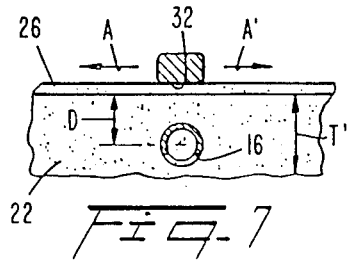

METHOD AND APPARATUS FOR PERFORMING SUCTION LIPECTOMY

RELATED APPLICATIONS

This application is a continuation-in-part of my copending U.S. patent application, Ser. No. 607,714, filed May 7, 1984, now U.S. Pat. No. 4,596,553, 06/24/86 and U.S. Ser. No. 651,720, filed Sept. 18, 1984, now U.S. Pat. No. 4,627,834, 12/09/86.

TECHNICAL FIELD

The present invention relates generally to surgical instruments and, more particularly, to a surgical cannula and its method of use in performing suction lipectomy to remove excessive accumulations of fatty tissue from a human body.

BACKGROUND ART

Suction lipectomy or lipolysis is a surgical procedure for removing fatty tissue and fatty tumors from localized areas of the human body through small incisions that can be easily concealed. The surgical procedure customarily employed requires an incision in the skin to expose the fatty tissue. The tip of a cannula is then inserted into the incision and manually directed by the surgeon towards the desired area of the body. By guiding the tip through the fatty tissue while simultaneously applying suction through a longitudinal passage extending through the cannula in communication with the tip, fat is surgically aspirated from the body. For adequate aspiration, approximately 15–20 strokes of the tip through the fatty tissue are often necessary.

FIG. 1 is an illustration of a conventional cannula 10 used for suction lipectomy having a tip 12 and a handle 14 formed at opposite ends thereof. Tip 10 has a hole 16 communicating with a central longitudinal passage 19 extending through the cannula for connection to a suction means 20 in a well known manner. To remove a desired amount of fat from fatty tissue 22 (see FIGS. 2 and 3), an incision 24 is first made in skin 26 to expose the tissue. Tip 10 is then inserted through incision 24 into tissue 26. By gripping handle 14 to move tip 12 through the fatty tissue in continuous reciprocating strokes (see arrows A and A') while applying suction, fat is surgically aspirated through hole 16 and passage 18. After a sufficient number of strokes by the surgeon, the original thickness T of fatty tissue is reduced to a lesser thickness T' (see FIG. 3A).

Because suction lipectomy is essentially cosmetic surgery, considerable surgical skill is necessary to repetitively guide tip 12 in directions A, A' to leave an even layer of tissue intact. This requires guiding tip 12 at a constant depth beneath the skin. Otherwise, different thicknesses of remaining tissue will cause permanent indentations 28 to appear in the skin following surgery (see FIG. 3A), which can be very unsightly. Unfortunately, however, the results frequently obtained with suction lipectomy are of the type shown in FIG. 3A, since the surgeon does not always know or cannot maintain the precise depth at which he guides tip 12 through the tissue. Further, since the surgeon must guide the tip in directions A,A', there is a tendency during the stroke to rotate (arrows B,B') the cannula about its longitudinal axis, causing hole 16 to move above or below the desired depth. Even if the surgeon possesses sufficient skill to guide tip 12 at constant depth, the large number of repetitive strokes necessary for adequate aspiration renders the surgical procedure fatiguing to the surgeon, possibly resulting in momentary loss of control while guiding the cannula.

It is equally important that the surgeon avoid excessive penetration of the cannula tip through the fatty tissue; otherwise, damage to vital organs can occur.

It is accordingly an object of the present invention to provide an improved cannula that is easily guided by the surgeon at a constant depth so that a desired amount of fatty tissue is surgically aspirated while leaving an even thickness layer of tissue intact.

Yet a further object is to provide a cannula that is easy for the surgeon to manipulate, rendering lipolysis less fatiguing to the surgeon to improve safety.

A further object is to provide a cannula that is simple in design and economical to manufacture.

Still another object is to provide a cannula having means preventing excessive penetration of the cannula tip into the body, avoiding possible damage to vital organs.

DISCLOSURE OF THE INVENTION

A device for surgically aspirating subcutaneous fatty tissue from an animate body, in accordance with a first embodiment of the invention, comprises a cannula having a tip and a handle at opposite ends thereof. The tip is formed with a hole in communication with a longitudinal passage extending through the cannula. The passage is connectible to a source of vacuum so that suction can be applied to surgically aspirate fatty tissue through the hole when the tip is implanted in tissue. A guide bar is attached to the cannula for maintaining the hole at a predetermined desired depth within the tissue as the tip is manually directed by a surgeon.

The guide bar preferably has one end connected to the cannula handle and an opposite free end terminating adjacent and spaced from the tip, with a guide surface facing the cannula. During surgery, this guide surface contacts the skin surface overlying the fatty tissue to control the depth at which the tip removes fat so that an even thickness layer of tissue remains intact upon completion of surgery.

In accordance with another aspect of the invention, the guide bar is preferably connected to the cannula handle with a hinge and nut/bolt arrangement. The nut is adjustable to vary the spacing between the guide surface and cannula tip to achieve a desired degree of penetration into fatty tissue. A wrench for manipulating the nut is formed with a body having stepped portions of predetermined, marked thickness functioning as measurement gauges to achieve the desired spacing.

In accordance with the method of the present invention, an incision is formed in the skin to expose the subcutaneous fatty tissue. The tip of the cannula is inserted through the incision until the guide surface contacts the skin. Suction is then applied while simultaneously moving the tip through the tissue in reciprocating strokes to surgically aspirate tissue, with proper depth achieved by maintaining the guide surface in contact with the skin. Lubricant may be applied to portions of the skin engageable with the guide surface to reduce friction.

In accordance with a second embodiment of the invention, the guide bar is formed with an elevated portion between opposite ends thereof. In operation, only the guide surface is in sliding contact with the skin surface to control the depth of cannula tip; the elevated portion is gripped by the surgeon and allows the surgeon to manually contact the skin beneath the elevated portion to assist in manipulation of the cannula.

In accordance with a third embodiment of the invention, wheels can be rotatably mounted to the free end of the guide bar to establish a low friction guide surface by virtue of rolling contact with the skin.

Still other objects of the present invention will become readily apparent to those skilled in this art from the following description wherein there is shown and described a preferred embodiment of this invention simply by way of illustration of one of the best modes contemplated for carrying out the invention. As will be realized, the invention is capable of other different embodiments, and its several details are capable of modifications in various, obvious respects, all without departing from the invention.

BRIEF DESCRIPTION OF THE DRAWING

FIG. 1 is a side elevational view of a conventional cannula commonly used to perform suction lipectomies;

FIG. 2 is a top view of an area of the body on which suction lipectomy is to be performed through an incision formed in the skin;

FIG. 3 is an enlarged fragmentary sectional view taken along the line 3—3 of FIG. 2 showing the tip of the prior art cannula of FIG. 1 inserted into the fatty tissue through the incision prior to surgical aspiration;

FIG. 3A is a view similar to FIG. 3 showing typical results obtained with the prior art cannula of FIG. 1 upon completion of the suction lipectomy;

FIG. 4 is a side elevational view of the cannula in accordance with a first embodiment of the present invention;

FIGS. 5 and 5A are sectional views taken respectively along the lines 5—5 and 5A—5A of FIG. 4 showing the positional relationship of the guide bar relative to the suction hole of the cannula and a plah view of the guide surface;

FIG. 6 is a sectional view taken along the line 6—6 of FIG. 4 of a mechanism for connecting as well as adjusting the spacing between the cannula and guide bar;

FIG. 7 is a view similar to FIG. 3A but showing the results of suction lipectomy obtained with the cannula of the present invention;

BEST MODE FOR CARRYING OUT THE INVENTION

Figure 8:
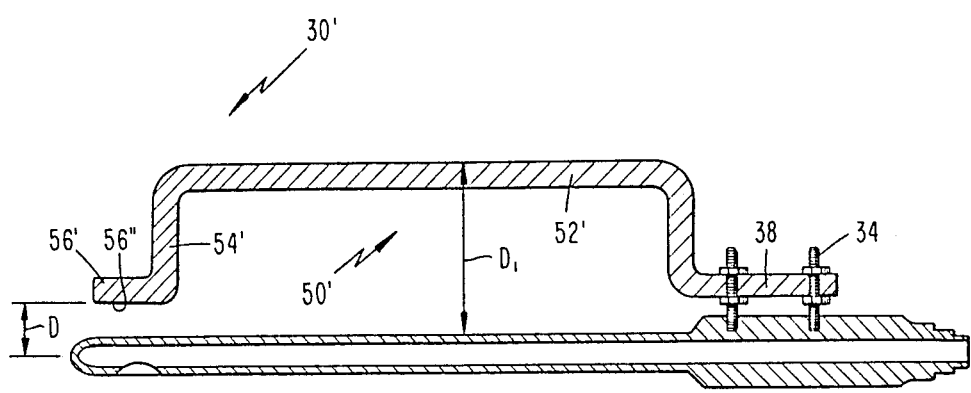
FIG. 8 is a side elevational view of a second embodiment of the cannula in accordance with the present invention.

In accordance with one embodiment of the present invention, cannula 10 includes a parallel guide bar 30 having a guide surface 32 pressed by the surgeon into constant contact with skin 24 so that suction hole 16 remains at constant depth during reciprocation of the cannula. The guide bar 30, preferably formed of medical grade stainless steel, is connected to cannula 10 with threaded bolts 34 secured to handle 14. Bolts 34 respectively pass through longitudinally spaced through holes 36 formed at one end 38 of bar 30 overlying the handle. The diameter of through holes 36 is larger than the external threaded diameter of bolts 34, enabling the guide bar to slide on the bolts to vary the spacing between the guide and cannula as discussed more fully below.

A pair of nuts 40a and 40b threaded onto each bolt 34 secure guide bar 30 to cannula 10 at a constant spacing C. To adjust the spacing between the cannula and guide bar, one of nuts 40a, 40b on each bolt 34 is loosened, enabling the bar to slide on the bolt. Thereafter, the other nut is tightened against the repositioned bar to lock same into the adjusted position.

Guide surface 32 may be formed at the free end 42 of guide bar 30 (FIGS. 4 and 5A) and is inclined upward from bar 30 to approximate the curvature of tip 12 and terminates short of the tip so that surface 32 overlies and is generally parallel to the mouth of cannula hole 16. In use, the guide surface 32 is positioned to rest upon skin 26 so that the cannula hole is embedded in tissue 22 at a predetermined desired depth C determined by the aforesaid nut and bolt arrangement. As best shown in FIG. 7, the hole 16 is maintained at constant depth by the surgeon during reciprocating movement of the cannula (in a plane perpendicular to FIG. 7) by virtue of guide surface 32 being easily pressed in sliding contacat with the skin. Thus, upon completion of the suction lipectomy, a uniform thickness layer T' (T'<T) remains intact so that skin 24 has an even, pleasing appearance.

Since cannula tip 10 is introduced into tissue 22 through incision 24 at an angle (not shown in detail), the guide surface 32 is easily positioned on the surface of skin 26 in overlying relation to cannula hole 16. Since the guide surface is preferably smooth and rectangular in area (FIG. 5A), this smooth surface estabishes a stable base that easily moves along the skin and resists any leveraging action tending to be imparted by the surgeon to the cannula tip during movement of handle 14. Thus, by applying a gentle downward pressure to ensure contact between surface 32 and skin 26, the guide surface provides a visual point of reference for the surgeon so that the cannula hole surgically aspirates fat at a constant depth.

The provision of guide surface 32 allows the surgeon to utilize both hands in gripping handle 14 to move cannula 10. Thus, the surgical procedure is less fatiguing to the surgeon.

To ensure that guide surface 32 slides smoothly along the surface of skin 26, a lubricant is preferably applied to the skin to reduce friction.

Referring now to FIG. 8 wherein a second embodiment of the cannula depicted in FIG. 4 is shown, a guide bar 30' of the present invention comprises a U-shaped elevated portion 50' having a main straight section 52' spaced a distance D1 from the cannula body. The distance D1 is sufficient to allow the surgeon to grip section 52' with one hand, for improved leverage, without contacting the patient's skin or cannula body. The distance D1 is also sufficient to enable the surgeon to place his hand under the section 52' on the patient's skin to manually stretch the skin or provide manual counterforce against the cannula during the suction lipectomy.

The forward end portion 54' of elevated portion 50' is offset 90° from section 52' towards the cannula and terminates in distal end or tip 56' (approximately 2-4 cm in length) having a lower guide surface 56" (similar to guide surface 32 in the first embodiment) that extends generally parallel to the cannula tip. In use, the guide surface 56" is positioned to rest upon skin 26 so that the cannula hole is embedded in tissue 22 at a predetermined desired depth C determined by the aforesaid nut and bolt arrangement. The cannula hole is maintained at constant depth by the surgeon during reciprocating movement of the cannula by virtue of guide surface 56" being easily pressed in sliding contact with the skin.

In the first embodiment depicted in FIG. 4, there exists a tendency for surface portions of guide bar 30 formed immediately adjacent guide surface 32 to contact the skin surface during the surgical procedure tending to increase frictional contact with the skin. However, by elevating a major portion 52' from the cannula body as in the second embodiment, only guide surface 56" remains in contact with the skin surface to facilitate reciprocating movement of the cannula through the fatty tissue. Furthermore, by providing guiding contact only through guide surface 56", it becomes easier to maintain the guide surface in contact with the skin when performing the surgical procedure on various parts and thereby different contours of the body (i.e., flat, concave or convex) since surface portions that are otherwise formed immediately adjacent the guide surface in the guide bar 30 of the first embodiment are not elevated away from the patient's skin.

Figure 9:
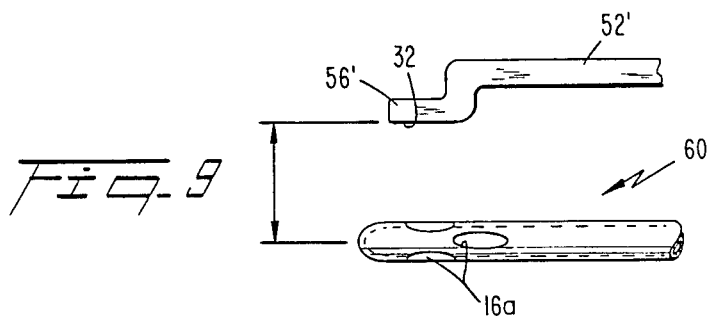
FIG. 9 is a view similar to FIG. 8 showing a further embodiment of the cannula according to the present invention.
Figure 10:
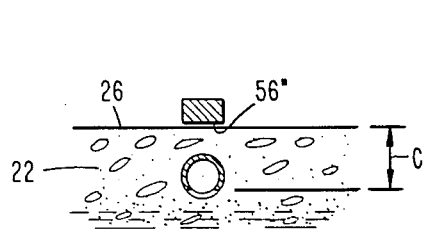
FIGS. 10 and 11 are enlarged fragmentary views showing the tip of the improved cannula of the second embodiment inserted into fatty tissue through an incision prior to surgical aspiration.
Figure 11:
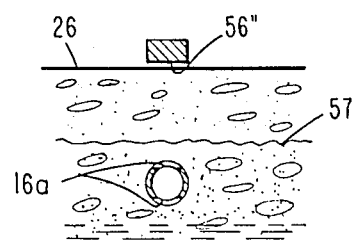

The elevated portion 50' also facilitates removal of deep fatty tissue from the abdominal wall, such as the layer of fatty tissue located beneath the Scarpa's fascia 57 as depicted in FIG. 11. Preferably, removal of the fatty tissue from the abdominal wall, such as the layer of fatty tissue located beneath the Scarpa's fascia 57 is facilitated by use of a multihole cannula 60 depicted in conjunction with guide bar 30' in FIG. 9. The overlying guide surface 56" provides positive control over the depth at which the cannula tip reciprocates to prevent deeper penetration and thereby avoid damage to internal organs. However, in removing the layer of fatty tissue below the Scarpa's fascia, it is not necessary to maintain contact between guide surface 56" and the patient's skin since the Scarpa's fascia situated above the cannula tip prevents excessive removal of fat.

Figure 12:
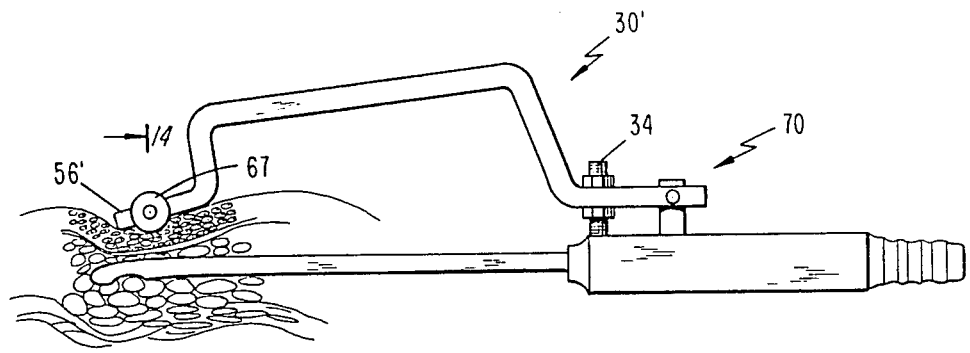
FIGS. 12 and 13 are side and top plan views of a third embodiment of the invention.
Figure 13:
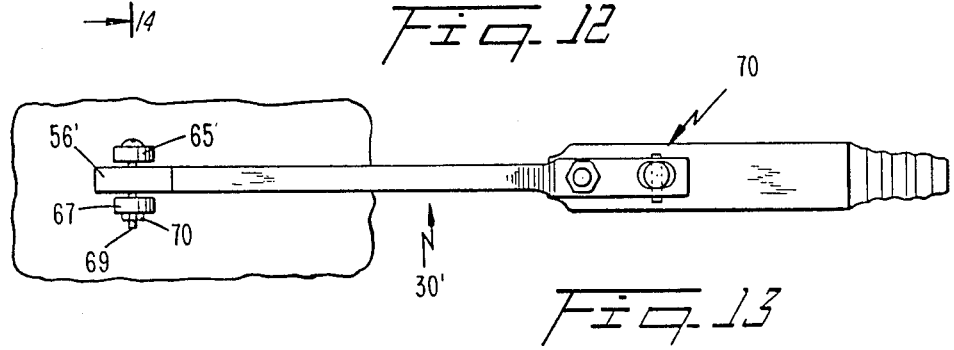
Figure 14:
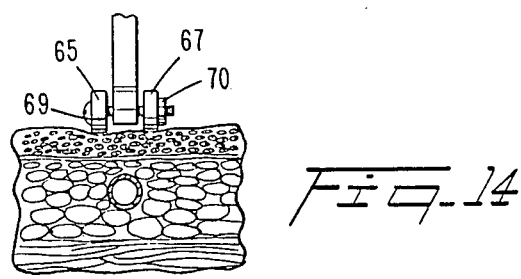
FIG. 14 is a sectional view taken along the line 14—14 of FIG. 12.

In accordance with a preferred embodiment of the invention depicted in FIG. 12, tip 56' of guide bar 30' preferably carries a pair of wheels 65,67 mounted to the tip with a cross bolt 69 and nut 70. Wheels 65,67 rotate freely on bolt 69 to provide tangential rolling contact with the skin surface for low friction movement during reciprocating strokes with the cannula. Wheels 65,67 are preferably one inch in diameter and approximately ¼ inch thick and are formed of stainless steel or any heat resistant material capable of withstanding heat from autoclaving without expanding.

Wheels 65,67 facilitate reciprocating stroking of the cannula for suction of fat and allow the cannula and guide bar to easily go around different contours of the body. Wheels 65,67 also stabilize the skin between the wheels and the underlying cannula.

In accordance with a further improvement to the preferred embodiment of the invention, rear bolt 34 is replaced with a hinge 70 to fix the guide bar to the cannula handle. Adjustment of the distance between the cannula and wheels 65,67 is thus facilitated vis-a-vis the dual nut and bolt arrangement depicted in FIG. 8 since distance can now be adjusted via manipulation of a single bolt and nut.

Figure 15:
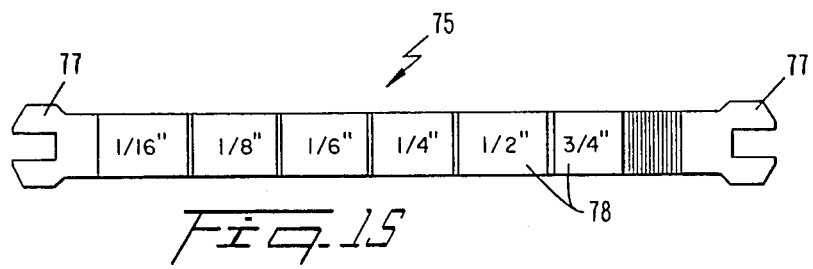
FIGS. 15 and 16 are top and side plan views, respectively, of an adjustment wrench used to adjust the spacing between the guide bar and cannula.
Figure 16:
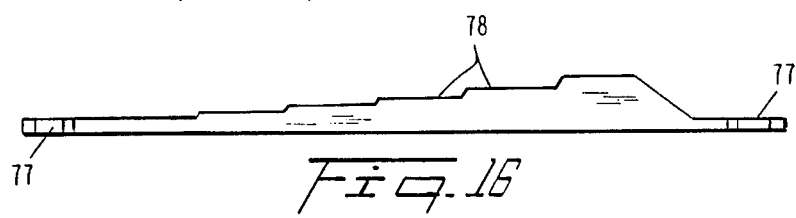

To effect proper, predetermined spacing between wheels 65,67 and the cannula body, a wrench 75 having either fixed or adjustable heads 77 is provided to adjust the nuts mounted on bolt 34. When adjusting the nuts, it will be understood that wheels 65,67 move towards or away from the cannula body to vary the spacing. To obtain a desired spacing between the wheels and cannula body, wrench 75, as shown in FIGS. 15 and 16, is preferably formed with stepped portions 78 of predetermined marked thickness. By passing one of the stepped portions 78 between wheels 65,67 and the cannula body, appropriate predetermined spacing is easily achieved since these stepped portions function as measurement gauges.

The foregoing description of the preferred embodiment of the invention has been presented for purposes of illustration and description. It is not intended to be exhaustive or to limit the invention to the precise form disclosed, and obviously many modifications and variations are possible in light of the above teaching. For example, the present invention can be practiced with cannulas formed with plural suction holes. Additionally, tip 12 need not necessarily be curved upward as discussed above; the cannula tip can be straight or curved downward, to accommodate different areas (or contours) of the body on which suction lipectomy is to be performed. However, for best results, free end 42 (i.e., surface 32 of guide 30) should be parallel (i.e., of similar curvature) to the cannula tip, unless wheels 65,67 are employed. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A device for surgically aspirating subcutaneous fatty tissue and the like from an animate body, comprising:
    (a) a cannula having a tip and a handle at opposite ends thereof, the tip being formed with a hole, and a longitudinal passage extending through the cannula in communication with the hole, said passage being connectable to a source of vacuum so that suction can be applied to surgically aspirate fatty tissue through the hole when the tip is inserted in the tissue;
    (b) guide means attached to the cannula for maintaining the hole at a predetermined depth within the tissue as the tip is manually directed by a surgeon through the tissue in reciprocating strokes, said guide means including a guide surface defined by guide wheel means in rolling contact with, during surgery, a portion of the skin overlying the fatty tissue to limit the depth at which the hole penetrates the tissue; and
    (c) means for connecting the guide means to the cannula.

2. The device of claim 1, wherein said guide means includes an elongate guide bar having one end connected to a portion of the cannula remote from the tip and an opposite free end terminating adjacent the hole in spaced relationship to the tip, said opposite free end having said guide surface.

3. The device of claim 2, wherein said opposite free end is spaced a first predetermined distance D from the tip, said opposite end having a guide surface in contact with, during surgery, a portion of the skin overlying the fatty tissue to limit the depth at which the hole penetrates the tissue, said guide bar including an elevated portion formed between the guide surface and the said one end of the guide bar and spaced a second predetermined distance D1 from portions of the cannula formed adjacent said elevated portion, wherein D1 is greater than D, said elevated portion being manually engageable by one hand of the surgeon while the surgeon's other hand engages the gripping portion of the cannula to thereby facilitate surgical manipulation of said device by the surgeon.

4. The device of claim 2, wherein said free end of the guide bar carries said guide wheel means including a pair of wheels defining said guide surface to provide low friction rolling contact with the skin during reciprocating strokes of the cannula.

5. The device of claim 2, wherein said guide surface is generally parallel to the mouth of the hole.

6. The device of claim 2, further including means for adjusting the spacing between the guide surface and cannula to thereby enable the surgeon to select the depth at which the hole will move through the tissue relative to the guide surface.

7. The device of claim 6, wherein said connecting means includes a nut and bolt connecting the guide bar to the handle, said bolt extending respectively through a hole formed in said one end of the guide bar in sliding contact therewith, and a pair of nuts threaded onto said bolt to contact opposite sides of the guide bar, said nuts coacting to adjust and maintain a desired spacing between the guide bar and cannula, and further including a hinge mounted adjuacent the nut and bolt for connecting the guide bar to the handle.

8. The device of claim 7, further comprising a wrench for adjusting said nuts to vary the spacing between the guide surface and cannula, said wrench formed with stepped gauge portions of known, marked thickness to obtain a desired predetermined spacing.

9. A method of surgically aspirating subcutaneous fatty tissue from desired areas of an animate body with the cannula having a tip and a handle at opposite ends thereof, the tip being formed with a hole, and a longitudinal passage extending through the cannula in communication with the hole, said passage being connected to a vacuum source so that suction is applied through the hole, said cannula supporting a guide member having a rolling surface defined by a rotatable structure attached to the guide member and spaced from the tip, comprising the steps of:
(a) forming an incision to expose said subcutaneous fatty tissue;
(b) inserting the tip of the cannula through the incision so that the hole contacts the fatty tissue and the guide surface rests on the skin;
(c) applying suction through the hole while simultaneously moving the tip through the tissue in reciprocating strokes to surgically aspirate tissue in contact with the hole; and
(d) guiding the hole within the tissue at a constant predetermined depth by maintaining the rolling guide surface in constant rolling contact with the skin while moving the tip through the tissue in said reciprocating strokes.

10. The method of claim 9, comprising the further step of applying a lubricant to portions of the rolling skin engageable with the guide surface to further reduce friction therebetween.

11. A device for positioning a tip of a cannula at a contant depth within subcutaneous fatty tissue to surgically aspirate the tissue upon application of suction supplied thereto through the tip, comprising guide means mounted on the cannula and spaced apart from said tip for maintaining said tip at said constant depth as the length of said cannula and tip is manually directed by a surgeon through the tissue in reciprocating strokes, said guide means including a guide surface spaced above and overlying the tip and located to remain in substantially constant contact with a portion of the skin covering the fatty tissue such that the cannula hole remains at substantially constant depth during the stroking movement; and means for connecting the guide means to the cannula, said guide surface being defined by guide wheel means in rolling contact with, during surgery, a portion of the skin overlying the fatty tissue to limit the depth at which the hole moves through the tissue.

12. The device of claim 11, wherein a peripheral surface of said guide wheel mean defining the rolling guide surface is spaced inwardly from an outermost end surface of said free end.

13. The device of claim 11, wherein said guide means includes an elongate guide bar having one end connected to as portion of the cannula remote from the tip and an opposite free end terminating adjacent the hole in spaced relationship to the tip, said opposite free end carrying said guide wheel means.

14. The device of claim 13, wherein said opposite free end is spaced a first predetermined distance D from the tip, said opposite free end having said rolling guide surface, said guide bar further including an elevated portion formed between the rolling guide surface and the said one end of the guide bar and spaced a second predetermined distance D1 from portions of the cannula formed adjacent said elevated portion, wherein D1 is greater than D, said elevated portion being manually engageable by one hand of the surgeon while the surgeon's other hand engages the gripping portion of the cannula to thereby facilitate surgical manipulation of said device by the surgeon.

15. A device for surgically aspirating subcutaneous fatty tissue and the like from an animate body, comprising:
(a) a cannula having a tip and a handle at opposite ends thereof, the tip being formed with a hole, and a longitudinal passage extending through the cannula in comunication with the hole, said passage being connectable to a source of vacuum so that suction can be applied to surgially aspirate and remove fatty tissue through the hole when the tip is inserted in the tissue;
(b) guide means attached to the cannula and spaced apart from said tip for maintaining the hole at a predetermined generally constant depth within the tissue as the length of said cannula and tip is manually directed by a surgeon through the tissue in reciprocating strokes with a guide surface of said guide means being in substantially constant contact with the surface of said skin overlying the fatty tissue during said strokes; and (c) means for connecting the guide means to the cannula, said connecting means including nut and screw means for securing the guide means to the cannula, and further comprising a wrench for adjusting said nut means to vary the spacing between the guide surface and cannula, said wrench formed with a stepped gauge portions of known, marked thickness to obtain a desired predetermined spacing.

16. A device for positioning a tip of a cannula at a constant depth within subcutaneous fatty tissue to surgically apsirate the tissue upon application of suction supplied thereto through the tip, comprising guide means mounted on the cannula and spaced apart from said tip for maintaining said tip at said constant depth as the length of said cannula and tip is manually directed by a surgeon through the tissue in reciprocating strokes, said guide means including a guide surface spaced above and overlying the tip and located to remain in substantially constant contact with a portion of the skin covering the fatty tissue such that the cannula hole remains at substantially constant depth during the stroking movement; said guide means including means for connecting the guide means to the cannula; and means for varying and adjusting the spacing between the guide surface and cannula tip, said adjusting means including a wrench formed with stepped gauge portions of known, marked thickness to obtain a desired predetermined spacing between the guide surface and cannula.

* * * * *